United States Patent [19]

Stadler

[11] 4,180,581
[45] Dec. 25, 1979

[54] N-9,10-DIHYDROLYSERGYL-M-AMINOBENZOIC ACID AMIDE DERIVATIVE

[75] Inventor: Paul Stadler, Biel-Benken, Switzerland

[73] Assignee: Sandoz Ltd., Basel, Switzerland

[21] Appl. No.: 872,639

[22] Filed: Jan. 26, 1978

[30] Foreign Application Priority Data

Jan. 28, 1977 [CH] Switzerland .................. 1070/77

[51] Int. Cl.² .................. C07D 457/06; A61K 31/48
[52] U.S. Cl. ...................... 424/261; 424/246; 424/248.54; 424/250; 544/60; 544/125; 544/361; 546/69
[58] Field of Search .............. 260/285.5; 424/261; 546/69

[56] References Cited

U.S. PATENT DOCUMENTS

| | | | |
|---|---|---|---|
| 3,228,942 | 1/1966 | Camerino et al. | 260/285.5 |
| 3,583,992 | 6/1971 | Hofmann et al. | 260/285.5 |
| 3,901,891 | 8/1975 | Fehr et al. | 260/285.5 |
| 3,904,633 | 9/1975 | Mago et al. | 424/261 |

*Primary Examiner*—Donald G. Daus
*Assistant Examiner*—Mary C. Lee
*Attorney, Agent, or Firm*—Gerald D. Sharkin; Robert S. Honor; Thomas O. McGovern

[57] ABSTRACT

The present invention provides compounds of formula I, wherein
  X is hydrogen, chlorine or bromine and
  Y is hydrogen or bromine, with the proviso that when X is chlorine Y is hydrogen,
  Z is carbonyl or sulphonyl,
  $R_1$ is alkyl of 1 to 4 carbon atoms, and
either (i)
  $R_2$ is hydrogen or alkyl of 1 to 5 carbon atoms, and
  $R_3$ is hydrogen, alkyl of 1 to 5 carbon atoms, or phenyl,
or (ii)
  $R_2$ together with $R_3$ is a radical of formula $$-\underset{R_5}{\underset{|}{\overset{R_4}{\overset{|}{C}}}}-(CH_2)_3-\underset{R_7}{\underset{|}{\overset{R_6}{\overset{|}{C}}}}-$$

wherein $R_4$, $R_5$, $R_6$ and $R_7$ are, independently, hydrogen or alkyl of 1 to 4 carbon atoms,
or (iii)
  $R_2$ together with $R_4$ is a radical of formula $$-(CH_2)_2-A-(CH_2)_2-$$

wherein A is a bond, oxygen, sulphur or $NR_8$ wherein $R_8$ is hydrogen, alkyl of 1 to 4 carbon atoms, phenyl or alkoxyphenyl, useful as venotonising agents.

21 Claims, No Drawings

N-9,10-DIHYDROLYSERGYL-M-AMINOBENZOIC ACID AMIDE DERIVATIVE

This invention relates to ergot derivatives.

The present invention provides compounds of formula I,

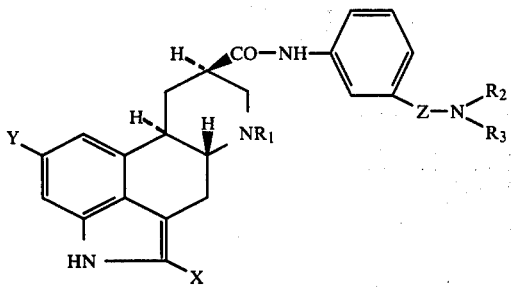

wherein
X is hydrogen, chlorine or bromine and
Y is hydrogen or bromine, with the proviso that when X is chlorine Y is hydrogen,
Z is carbonyl or sulphonyl,
$R_1$ is alkyl of 1 to 4 carbon atoms, and
either (i)
$R_2$ is hydrogen or alkyl of 1 to 5 carbon atoms, and
$R_3$ is hydrogen, alkyl of 1 to 5 carbon atoms, or phenyl,
or (ii)
$R_2$ together with $R_3$ is a radical of formula

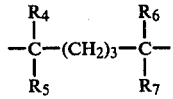

wherein $R_4$, $R_5$, $R_6$ and $R_7$ are, independently, hydrogen or alkyl of 1 to 4 carbon atoms,
or (iii)
$R_2$ together with $R_3$ is a radical of formula

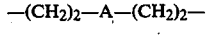

wherein A is a bond, oxygen, sulphur or $NR_8$ wherein $R_8$ is hydrogen, alkyl of 1 to 4 carbon atoms, phenyl or phenyl monosubstituted by alkoxy of 1 to 4 carbon atoms.

Z is preferably carbonyl.

$R_1$ is conveniently methyl, or isopropyl or sec-butyl. When X and Y are each hydrogen and $R_2$ and/or $R_3$ are alkyl, then preferably at least one of $R_2$ and $R_3$ is alkyl of 2 or more carbon atoms, e.g. ethyl or isopropyl. When X and Y are each other than hydrogen and $R_2$ and/or $R_3$ is alkyl this is conveniently methyl or isopropyl. Preferably $R_2$ and $R_3$ are the same.

Preferably $R_4$ is the same as $R_5$, and $R_6$ is the same as $R_7$. It is also preferred that $R_4$, $R_5$, $R_6$ and $R_7$ are identical. When $R_4$, $R_5$, $R_6$ and/or $R_7$ is alkyl, this is preferably methyl or ethyl. A is conveniently a group $NR'_8$ wherein $R_8'$ is phenyl, alkoxyphenyl or preferably alkyl, especially methyl.

When $R_8$ is alkoxyphenyl, this is conveniently methoxyphenyl or ethoxyphenyl.

Preferably $R_2$ and $R_3$ are chosen from hydrogen or alkyl or are together a radical $-(CH_2)_2-A-(CH_2)_2-$.

The present invention provides a process for the production of a compound of formula I as defined above, which comprises condensing a reactive functional acid derivative of a compound of formula II,

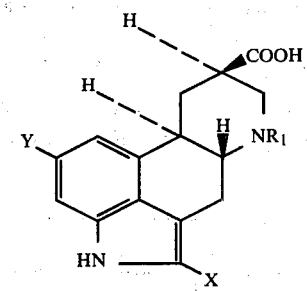

Wherein X, Y and $R_2$ are as defined above, with a compound of formula III,

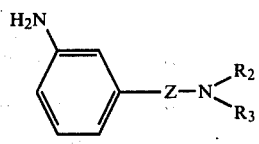

wherein Z, $R_2$ and $R_3$ are as defined above.

The process may be effected in conventional manner for the production of analogous lysergic acid amides by condensation reactions.

As the reactive functional acid derivative of a compound of formula II may be used the acid chloride, the acid azide, or a mixed anhydride of an acid of formula II with sulphuric or trifluoroacetic acid, or preferably the reaction product of a compound of formula II with oxalyl chloride in the presence of dimethylformamide.

The starting materials are known or may be made in conventional manner.

Free base forms of the compounds of formula I may be converted into acid addition salt forms in conventional manner and vice versa. A suitable acid for salt formation is maleic acid, methanesulphonic acid, phosphoric acid, tartaric acid or hydrochloric acid.

In the following examples all temperatures are in degrees centigrade and are uncorrected.

EXAMPLE 1

N-9,10-dihydrolysergyl-m-aminobenzoic acid diethylamide 12.9 g Oxalyl chloride in 40 ml absolute acetonitrile are added dropwise over 20 minutes to a mixture of 125 ml absolute dimethylformamide and 75 ml absolute acetonitrile cooled to −15° to −20°. After the mixture is stirred for 10 minutes, 40.5 g of 9,10-dihydrolysergic acid are added. The mixture is stirred for a further ½ hour at 0° and then cooled to −10° to −15°. 75 ml pyridine and then 19.1 g m-aminobenzoic acid diethylamide are added. The mixture is stirred for 2½ hours, poured onto 300 ml of an aqueous 2 N sodium carbonate solution and extracted three times with methylene chloride. The combined organic phases after one washing with aqueous sodium carbonate are evaporated and the residue is quickly chromatographed on aluminium oxide to yield the title compound in free base form, m.p. 138°–141° (from saturated aqueous ethyl acetate).

Methanesulphonate: 8 g of the base in ethanol are treated with 18 ml 1 N methanesulphonic acid in ethanol. The methanesulphonate crystallises out, is filtered off, washed with ethanol and dried. M.P. 228°-230° (decomp.) $[\alpha]_D^{20} = -72°$ (c=1, dimethylformamide).

The starting material, m-aminobenzoic acid diethylamide (m.p. 80°-81°) is obtained by treating m-nitrobenzoyl chloride with diethylamine and catalytically hydrogenating over palladium on charcoal (10% by weight Pd) the resultant m-nitrobenzoic acid diethyl amide (m.p. 68°-70°).

In analogous manner to that described in Example 1, the following compounds of formula I may be obtained:

-continued

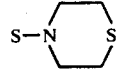  c)

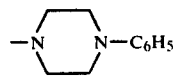  d)

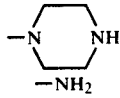  e)

—NH$_2$  f)

| Ex. No. | X | Y | Z | R$_1$ | R$_2$ | R$_3$ | M.Pt.[1]/[α]$_D^{20}$ [11] |
|---|---|---|---|---|---|---|---|
| 2 | H | H | SO$_2$ | CH$_3$ | CH$_3$ | CH$_3$ | 150°-152°[3]/−116° (c = 1,02) |
| 3 | H | H | CO | CH$_3$ | —(CH$_2$)$_2$—N(CH$_3$)—(CH$_2$)$_2$— | | 163°-165°[3]/−112° (c = 1,00) |
| 4 | H | H | CO | CH$_3$ | —(CH$_2$)$_2$—N(4-C$_6$H$_4$—OCH$_3$)—(CH$_2$)$_2$— | | from 82°[4]/−80,2° (c = 1,02) |
| 5 | H | H | CO | CH$_3$ | —CH(CH$_3$)$_2$ | CH(CH$_3$)$_2$ | 274°-276°[3]/−93.4° (c = 1,04) |
| 6 | H | H | SO$_2$ | CH$_3$ | CH(CH$_3$)$_2$ | CH(CH$_3$)$_2$ | 118°-190°[3]/−105° (c = 1) |
| 7 | H | H | CO | CH$_3$ | H | CH$_3$ | 154°-156°[3]/−85.2° (c = 1,8)[12] |
| 8 | H | H | CO | CH$_3$ | CH(CH$_3$)$_2$ | H | 203°-205°[5]/−77.3° (c = 1,8)[12] |
| 9 | H | H | CO | CH$_3$ | CH$_3$ | CH$_3$ | 204°-205°[2] [3]/−61.3° (c = 1)[14] |
| 10 | H | H | CO | CH$_3$ | CH$_3$ | C$_6$H$_5$ | 185°-188°[3]/−67.2° (c = 2)[12] |
| 11 | Br | Br | CO | CH$_3$ | CH$_3$ | CH$_3$ | 182°-185°[6]/−60,6° (c = 0.9)[13] |
| 12 | Cl | H | CO | CH$_3$ | CH$_3$ | CH$_3$ | 168°[6]/−101° (c = 0,76) |
| 13 | Br | H | CO | CH$_3$ | CH$_3$ | CH$_3$ | 166°-168°[3]/−139° (c = 0,99) |
| 14 | H | Br | CO | CH$_3$ | CH$_3$ | CH$_3$ | 197°-198°[3]/−90,6°(c = 1.03) |
| 15 | Br | Br | CO | CH$_3$ | CH(CH$_3$)$_2$ | CH(CH$_3$)$_2$ | from 230°[7]/−71.5° (c = 1.0) |
| 16 | Br | Br | CO | CH$_3$ | H | CH$_3$ | 290°-292°[2][3]/−102° (c = 1) |
| 17 | Br | Br | CO | CH$_3$ | CH$_3$ | C$_6$H$_5$ | 239°-242°[2] [8]/−121° (c = 2) |
| 18 | Br | Br | CO | CH$_3$ | —(CH$_3$)$_2$—(CH$_2$)$_3$—C(CH$_3$)$_2$— | | 208°-210°[2] [3]/−88.3° (c = 1) |
| 19 | Br | Br | SO$_2$ | CH$_3$ | CH(CH$_3$)$_2$ | CH(CH$_3$)$_2$ | 275°-277°[5]/−82.4° (c = 1) |
| 20 | H | H | CO | CH(CH$_3$)$_2$ | CH$_3$ | CH$_3$ | 183°-186°[4]/−113° (c = 0.93) |

[1]M.Pt is decomposition point except where marked [2]
[3]is free base
[4]is demi tartrate containing per mole 1 mole of water
[5]is methanesulphonate
[6]is hydrogen maleate
[7]is dihydrogen phosphate
[8]is hydrochloride
[11][α]$_D^{20}$ in pyridine except when marked [12] in dimethyl formamide or [1] in methanol or [14] in ethanol.

In analogous manner to that described in formula I the following compounds of formula I may be obtained wherein R$_1$ is ethyl, X and Y are each hydrogen, Z is SO$_2$ and NR$_2$R$_3$ is:

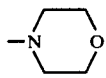  a)

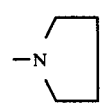  b)

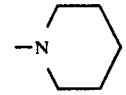  g)

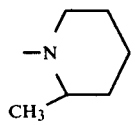  h)

The compounds exhibit venoconstricting activity as indicated by standard tests, e.g. by a pressoric effect and a blood pressure rise in the pithed rat on administration of from 0.001 to 1 mg/kg i.v. of the compounds according to the principles of Gillespie and Muir, Brit. J. Pharmacol. 30, 78–87 (1967).

The compounds are therefore useful as venotonising agents, e.g. for the treatment of orthostatic hypotension such as postural orthostasis and migraine.

For this use the dosage will, of course, vary depending on the compound employed, mode of administration and treatment desired. However, in general, satisfactory results are obtained when administered at a daily dosage of from about 0.001 mg to about 5 mg per kg animal body weight, conveniently given in divided doses 2 to 4 times a day or in sustained release form. For the larger mammals, the total daily dosage is in the range from about 0.15 to about 150 mg (e.g. from 0.5 to 10 mg), and dosage forms suitable for oral administration comprise from about 0.04 to about 75 mg of the compounds admixed with a solid or liquid pharmaceutical carrier or diluent.

The Example 1 compound is the preferred compound.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutically carrier or diluent.

Such compositions may be in the form of, for example, a solution or a tablet.

In a group of compounds $R_4$, $R_5$, $R_6$ and $R_7$ are identical and each are either hydrogen or methyl.

In a first group of compounds Z is carbonyl.

In a second group of compounds Z is sulphonyl.

In a third group of compounds $R_2$ and $R_3$ are defined as significance (i) stated above with respect to formula I. In a first sub-group $R_3$ is hydrogen or alkyl. In a second sub-group $R_3$ is phenyl.

In a fourth group of compounds $R_2$ and $R_3$ are defined as significance (ii) stated above with respect to formula I.

In a fifth group of compounds $R_2$ and $R_3$ are defined as significance (iii) stated above with respect to formula I. In a first sub-group A is a bond. In a second sub-group A is O. In a third sub-group A is S. In a fourth sub-group A is $NR_8$.

I claim:

1. A compound of formula I,

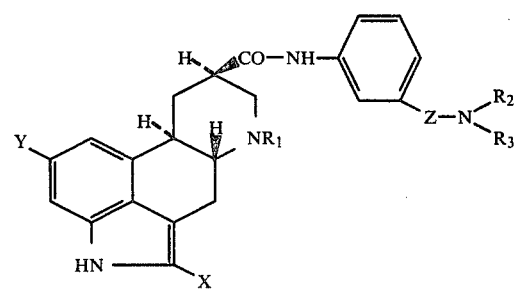

wherein
X is hydrogen, chlorine or bromine and
Y is hydrogen or bromine, with the proviso that when X is chlorine Y is hydrogen, Z is carbonyl or sulphonyl,
$R_1$ is alkyl of 1 to 4 carbon atoms, and
either (i)
$R_2$ is hydrogen or alkyl of 1 to 5 carbon atoms, and
$R_3$ is hydrogen, alkyl of 1 to 5 carbon atoms, or phenyl,
or (ii)
$R_2$ together with $R_3$ is

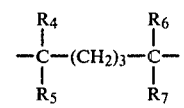

wherein $R_4$, $R_5$, $R_6$ and $R_7$ are, independently, hydrogen or alkyl of 1 to 4 carbon atoms,
or (iii)
$R_2$ together with $R_3$ is

wherein A is a bond,
or a pharmaceutically acceptable acid addition salt thereof.

2. A pharmaceutical composition useful in the treatment of orthostatic hypotension or migraine comprising a therapeutically effective amount of a compound of claim 1 in association with a pharmaceutical carrier of diluent.

3. A method of treating orthostatic hypertension or migraine in animals, which comprises administering a therapeutically effective amount of a compound of claim 1, to an animal in need of such treatment.

4. The compound of claim 1 which is N-9,10-dihydrolysergyl-m-aminobenzoic acid diethylamide.

5. The compound according to claim 1 in which X, Y, Z, $R_1$, $R_2$ and $R_3$ are H, H, $SO_2$, $CH_3$, $CH_3$, and $CH_3$ respectively.

6. The compound according to claim 1 in which X, Y, Z, $R_1$, $R_2$ and $R_3$ are H, H, CO, $CH_3$, $CH(CH_3)_2$ and $CH(CH_3)_2$ respectively.

7. The compound according to claim 1 in which X, Y, Z, $R_1$, $R_2$ and $R_3$ are H, H, $SO_2$, $CH_3$, $CH(CH_3)_2$ and $CH(CH_3)_2$ respectively.

8. The compound according to claim 1 in which X, Y, Z, $R_1$, $R_2$ and $R_3$ are H, H, CO, $CH_3$, H and $CH_3$ respectively.

9. The compound according to claim 1 in which X, Y, Z, $R_1$, $R_2$ and $R_3$ are H, H, CO, $CH_3$, $CH(CH_3)_2$ and H respectively.

10. The compound according to claim 1 in which X, Y, Z, $R_1$, $R_2$ and $R_3$ are H, H, CO, $CH_3$, $CH_3$ and $CH_3$ respectively.

11. The compound according to claim 1 in which X, Y, Z, $R_1$, $R_2$ and $R_3$ are H, H, CO, $CH_3$, $CH_3$ and $C_6H_5$ respectively.

12. The compound according to claim 1 in which X, Y, Z, $R_1$, $R_2$ and $R_3$ are Br, Br, CO, $CH_3$, $CH_3$ and $CH_3$ respectively.

13. The compound according to claim 1 in which X, Y, Z, $R_1$, $R_2$ and $R_3$ are Cl, H, CO, $CH_3$, $CH_3$ and $CH_3$ respectively.

14. The compound according to claim 1 in which X, Y, Z, $R_1$, $R_2$ and $R_3$ are Br, H, CO, $CH_3$, $CH_3$ and $CH_3$ respectively.

15. The compound according to claim 1 in which X, Y, Z, $R_1$, $R_2$ and $R_3$ are H, Br, CO, $CH_3$, $CH_3$ and $CH_3$ respectively.

16. The compound according to claim 1 in which X, Y, Z, $R_1$, $R_2$ and $R_3$ are Br, Br, CO, $CH_3$, $CH(CH_3)_2$ and $CH(CH_3)_2$ respectively.

17. The compound according to claim 1 in which X, Y, Z, $R_1$, $R_2$ and $R_3$ are Br, Br, CO, $CH_3$, H and $CH_3$ respectively.

18. The compound according to claim 1 in which X, Y, Z, $R_1$, $R_2$ and $R_3$ are Br, Br, CO, $CH_3$, $CH_3$ and $C_6H_5$ respectively.

19. The compound according to claim 1 in which X is Br, Y is Br, Z is CO, $R_1$ is $CH_3$ and $R_2$ and $R_3$ together are $-C(CH_3)_2-(CH_2)_3-C(CH_3)_2$ respectively.

20. The compound according to claim 1 in which X, Y, Z, $R_1$, $R_2$ and $R_3$ are Br, Br, $SO_2$, $CH_3$, $CH(CH_3)_2$ and $CH(CH_3)_2$ respectively.

21. The compound according to claim 1 in which X, Y, Z, $R_1$, $R_2$ and $R_3$ are H, H, CO, $CH(CH_3)_2$, $CH_3$ and $CH_3$ respectively.

* * * * *

UNITED STATES PATENT AND TRADEMARK OFFICE
CERTIFICATE OF CORRECTION

PATENT NO. : 4,180,581
DATED : Dec. 25, 1979
INVENTOR(S) : Paul Stadler

It is certified that error appears in the above—identified patent and that said Letters Patent is hereby corrected as shown below:

Claim 3, Column 6, delete the word "hypertension" and insert in its place the word -- hypotension --.

Signed and Sealed this

Nineteenth Day of August 1980

[SEAL]

Attest:

SIDNEY A. DIAMOND

Attesting Officer — Commissioner of Patents and Trademarks